(12) United States Patent
Heishi et al.

(10) Patent No.: US 6,280,951 B1
(45) Date of Patent: Aug. 28, 2001

(54) METHOD FOR PREDICTION OF PTH REACTIVITY BY POLYMORPHISM OF PTHR GENE

(75) Inventors: Masayuki Heishi; Osamu Ishida; Hiromitsu Tazawa, all of Sagamihara; Yusuke Tsukamoto, 280-6, Gumyoji-cho, Minami-ku, Yokohama-shi, Kanagawa, all of (JP)

(73) Assignees: Yusuke Tsukamoto, Yokohama; Sumikin Bio-Science, Inc., Sagamihara, both of (JP)

(*) Notice: Subject to any disclaimer, the term of this patent is extended or adjusted under 35 U.S.C. 154(b) by 0 days.

(21) Appl. No.: 09/521,656

(22) Filed: Mar. 8, 2000

(30) Foreign Application Priority Data

Mar. 9, 1999 (JP) ................................. 11-061774

(51) Int. Cl.[7] .............................. C12Q 1/68; C07H 21/04
(52) U.S. Cl. ........................... 435/6; 536/23.1; 536/24.3; 536/24.33
(58) Field of Search ............................... 435/6; 536/23.1, 536/24.33, 24.3

(56) References Cited

PUBLICATIONS

Schipani et al "Polymorphism in exon M7 of the PTHR gene" Human Molecular Genetics, vol. 3, No. 7, p. 1210, 1994.*

Hustmyer et al "Bsml polymorphism at the parathyroid hormone receptor locus (PTHR) in three populations" Human Molecular Genetics, vol. 2, No. 8, p. 1330, 1993.*

Schipani et al "Pseudohypoparathroidism Type lb is not caused by mutations in the coding exons of the human PTH/PTH–related peptide receptor gene" J. of Clinical Endocrinology and Metabolism, vol. 80, No. 5, p. 1611–1621, 1995.*

Heishi et al "A novel Nan91 ! polymorphism in the 1st intron of the parathyroid hormone" Biol. Pharm, Bill, vol. 23, No. 4, p. 386–389, Apr. 2000.*

Y. Tsukamoto et al, *Nature Medicine*, 2(11):1162 (1996).

F. Hustmyer et al., *Human Molecular Genetics*, 2(8):1330 (1993).

E. Schipani et al., *Human Molecular Genetics*, 3(7):1210 (1994).

* cited by examiner

*Primary Examiner*—Lisa B. Arthur
*Assistant Examiner*—Jeanine Goldberg
(74) *Attorney, Agent, or Firm*—Burns, Doane, Swecker & Mathis, LLP

(57) ABSTRACT

A method for predicting reactivity to parathyroid hormone by determining the genotype with respect to polymorphism in the parathyroid hormone receptor gene. The results obtained by the analysis of genetic polymophism are useful for predicting the tendency for a hemodialyzed patient to develop severe secondary hyperparathyroidism, or for predicting the tendency for a human individual to develop severe primary hyperparathyroidism. Also, this method is useful for predicting the therapeutic effects by predicting reactivity to parathyroid hormone in a patient who is being treated for regressive osteoporosis by administration of parathyroid hormone.

7 Claims, 1 Drawing Sheet

Ma: λ/HindIII digest marker

METHOD FOR PREDICTION OF PTH REACTIVITY BY POLYMORPHISM OF PTHR GENE

TECHNICAL FIELD

The present invention relates to a method for predicting reactivity to parathyroid hormone in humans by analysis of genetic polymorphism. The results obtained by the analyis of genetic polymorphism can be used in predicting the severity of secondary hyperparathyroidism in hemodialyzed patients, and the severity of primary hyperparathyroidism, and in predicting the effects of the administration of parathyroid hormone on treatment of regressive osteoporosis.

BACKGROUND OF THE INVENTION

Parathyroid hormone (hereinafter referred to as PTH) is a polypeptide hormone which is produced in the parathyroid gland and secreted therefrom. The main function of this hormone is to keep the calcium level in body fluids constant. PTH promotes bone resorption and calcium resorption in the kidney, thereby increasing the calcium level in blood, and PTH also promotes excretion of phosphate, thereby decreasing the phosphate level in blood. A decrease in the calcium level in blood promotes PTH secretion, while an increase in the calcium level in blood suppresses the secretion of PTH.

Hyperparathyroidism, which is characterized by excess secretion of PTH, includes primary and secondary hyperparathyroidism. In primary hyperparathyroidism, excess secretion of PTH due to tumefaction of the parathyroid gland, etc. results in dysbolism of calcium, thereby causing disorders such as hypercalcemia, hypophosphatemia, osteitis fibrosa, nephrolithiasis, and hypertension. Secondary hyperparathyroidism is caused when a low serum calcium level continues for a long time, which condition results from decreased renal function, deficiency of activated vitamin D, decreased reactivity of bones to PTH, etc. Secondary hyperparathyroidism results in an increase in PTH secretion. In some cases, this excess secretion of PTH continues even when the serum calcium level becomes normal or elevated, and may result in hyperparathyroidism becoming serious. For example, in a patient who is subjected to hemodialysis because of chronic renal failure, hyperparathyroidism tends to be serious. One of the important factors affecting this tendency is development of resistance to PTH, which is considered to be associated with reactivity to PTH. At present, secondary hyperparathyroidism is treated by the administration of activated vitamin $D_3$.

The severity of secondary hyperparathyroidism in hemodialyzed patients varies among individuals, and therefore genomic factors have become of interest. As an example of studies on genomic factors, there is a report which shows the relationship in Japanese between polymorphism of the vitamin D receptor (VDR) gene by restriction enzyme Bsm I and the serum PTH level in hemodialyzed patients (Y. Tsukamoto et al., Nature Med. vol.2, 1996, p. 1162). Polymorphism of the VDR gene is correlated with occurrence of secondary hyperparathyroidism and response to treatment with vitamin D. Also, severity of primary hyperparathyroidism is thought to be associated with the same genomic factors in some cases.

With respect to the mechanism of occurrence of hyperparathyroidism, genetic differences in reactivity to PTH have been thought to be a stronger determining factor. However, a methodology has not been established for examining genetic polymorphism to predict reactivity to PTH.

Polymorphism of the parathyroid hormone receptor gene was reported by Frank G. Hustmyer et al. in Human Mol. Gent. vol. 2, p. 1330 (Bsm I polymorphism) and by E. Schipani et al in Human Mol. Gent. vol. 3, p. 1210 (polymorphism in exon M7). However, there is no report demonstrating the polymorphism associated with PTH reactivity.

As mentioned above, a method for predicting PTH reactivity by analysis of genetic polymorphism has not been found, PTH reactivity being thought to be associated with severity of hyperparathyroidism, and predicting the severity thereof was difficult. The prediction of the severity of hyperparathyroidism is advantageous. For example, if a tendency for secondary hyperparathyroidism observed in hemodialyzed patients to become serious is predicted, a suitable method for treatment can be selected so as to prevent it from becoming serious. Alternatively, if the severity of symptoms accompanied by primary hyperparathyroidism such as hypercalcemia, bone lesions, urinary calculus, etc. is predicted, it may be possible to determine whether an operation for removal of the parathyroid gland should be performed and to determine how urgent the operation is. Furthermore, the prediction of PTH reactivity is useful for predicting the effects of PTH administration in the treatment of regressive osteoporosis.

SUMMARY OF THE INVENTION

Accordingly, an object of the present invention is to provide a method for predicting PTH reactivity by analysis of genetic polymorphism.

The present inventors have found the effects of genetic polymorphism of the parathyroid hormone receptor gene on the severity of hyperparathyroidism, and the relationship between this genetic polymorphism and PTH reaction, and have thereby completed the present invention.

The present invention provides a method for predicting reactivity to parathyroid hormone by determining a genotype with respect to genetic polymorphism of the parathyroid hormone receptor gene.

The determination of genotype may be performed by detection for the presence or absence of digestion with a restriction enzyme. In a preferred embodiment, genetic polymorphism is analyzed by treating a DNA fragment obtained by amplifying the first intron region of the parathyroid hormone receptor gene with restriction enzyme Van91 I. Preferably, amplification is performed using a primer having the sequence of SEQ ID NO:1 and a primer having the sequence of SEQ ID NO:2.

The present invention also provides a primer set for analyzing genetic polymorphism of the parathyroid hormone receptor gene, comprising a primer having the sequence of SEQ ID NO:1 and a primer having the sequence of SEQ ID NO:2, and furthermore provides a kit for prediction of reactivity to parathyroid hormone in a humany, comprising the above primer set and restriction enzyme Van91 I.

Furthermore, the present invention relates to a method for predicting the tendency for a patient being subjected to hemodialysis to suffer from severe secondary hyperparathyroidism according to the above-mentioned method, and a method for predicting the tendency for a human to suffer from severe primary hyperparathyroidism according to the analysis of polymorphism as mentioned above. Also, the present invention relates to a method for predicting the reactivity to parathyroid hormone to be administered for treatment of regressive osteoporosis according to the above-mentioned method.

DETAILED DESCRIPTION OF THE PREFERRED EMBODIMENTS

Figure 1:
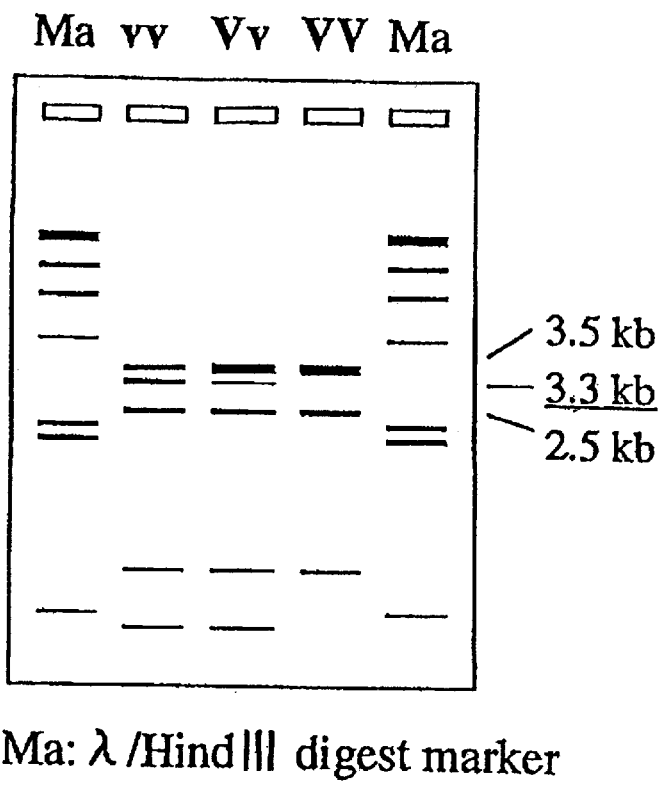
FIG. 1 shows digestion patterns of the PTHR gene with restriction enzyme Van91 I.

Parathyroid hormone exerts a hormone action by binding to the PTH receptor (PTHR) on cell membrane of bone or renal tubule. The present inventors have found that PTH reactivity is determined by the PTHR gene, and therefore it is presumed that PTH reactivity depends on the reactivity of the receptor.

The determination of PTH reactivity may be performed by the Ellsworth-Howard test. The principle of this test is as follows: The action of PTH on the PTH receptor on the cell membrane of renal tubules results in activation of adenylate cyclase, which increases intracellular cAMP, thereby enabling a hormone action to be exerted through PKA pathway. Therefore, the difference in cAMP concentrations in urine before and after the administration of PTH is the indicator of PTH reactivity. That is to say, when the difference in cAMP is large, it means a high PTH reactivity.

Samples used for the determination of genotype can be obtained from any body samples which contain DNA. However, white blood cells are preferred because of ease of collection. Various tissues also may be used.

Genetic polymorphism of the parathyroid hormone receptor gene may be analyzed by amplifying a selected region of the PTHR gene, treating the amplified DNA fragment with a particular restriction enzyme, and determining the genotype by digestion patterns. The PTHR gene exists on chromosome 3, and the nucleotide sequence thereof is known. Primers are designed for amplifying the desired region based on the data of the known sequence. In carrying out the present invention, for example, the first intron region of PTHR gene is amplified. As a primer pair therefor, primer A and primer B shown in the following example are preferred, and about 10 kb amplified DNA can be obtained by using this primer pair. The amplification of a selected region of the gene may be performed by the polymerase chain reaction (PCR) technique, etc., and the procedure used for the amplification may be conventional.

Amplified DNA product is treated with a restriction enzyme such as Van91 I. The amplified DNA fragment of the first intron region may be digested with this restriction enzyme, and then may be fractionated by a suitable mean such as electrophoresis and then identified. Such procedures may be carried out by conventional means, such as by agarose gel electrophoresis, staining with ethidium bromide, and exposure by UV radiation so as to display DNA bands, and the obtained digestion pattern can then be analyzed.

When the DNA fragment amplified using primer A and primer B is treated with Van91 I, an allele which is not cleaved is referred to as "V", and an allele which is cleaved is referred to as "v". Genotypes determined by the combination of these alleles include VV, Vv, and vv. The relationship between genotype and PTH reactivity can be examined by measuring the cAMP concentration before and after the administration of PTH in each group, the obtained difference being an indicator of PTH reactivity.

Furthermore, the intact PTH level in serum of hemodialyzed patients having genotype VV or Vv was found to be significantly higher than in genotype vv. This means that hemodialyzed patients having genotype VV or Vv are likely to develop serious secondary hyperparathyroidism.

Thus, the analysis of genetic polymorphism of the PTHR gene enables the prediction of PTH reactivity, and the prediction of the severity of secondary hyperparathyroidism in hemodialyzed patients. Therefore, a suitable therapeutic method can be selected in the earlier stage of hemodialysis. Also, it is possible to predict the severity not only in secondary hyperparathyroidism but also in primary hyperparathyroidism. Furthermore, this prediction of PTH reactivity enables a prediction of the effects of PTH administered for treatment of regressive osteoporosis, and therefore is useful for selecting a suitable therapeutic method.

The following examples are given to further illustrate the present invention, but it should be understood that the present invention is not limited to the specific details set forth in the examples.

EXAMPLE

The procedures for the analysis of genetic polymorphism, i.e., DNA extraction procedure, DNA amplification procedure, treatment with a restriction enzyme, electrophoresis, and determination of genotype, are as follows.

(1) DNA Extraction Procedure

The extraction of genomic DNA is carried out using a DNA extraction kit, Mag Extractor-Genome-(TOYOBO) in accordance with the appended information as follows:

1. 100 µl of whole blood (2Na-EDTA anticoagulant is used) are placed into a 1.5 ml microcentrifuge tube.
2. 750 ml of dissolving and adsorbing solution are added to the tube and mixed by a mixer several times.
3. 40 µl of silica-coated magnetic particles are added and mixed by a mixer for 10 minutes.
4. The particles are separated by a magnet stand and the supernatant is removed.
5. 900 µl of washing solution is added and mixed by a mixer for 10 seconds.
6. The particles are separated by a magnet stand and the supernatant is removed.
7. Steps 5 and 6 are repeated.
8. 900 µl of 70% ethanol is added and mixed by a mixer for 10 seconds.
9. The particles are separated by a magnet stand and the supernatant is removed.
10. Steps 8 and 9 are repeated.
11. After centrifugation (5,000 g, for 10 seconds at room temperature), supernatant is removed.
12. 100 µl of sterilized distilled water are added and mixed by a mixer for 10 minutes.
13. The particles are separated by a magnet stand and then supernatant is placed into another 1.5 ml microcentrifuge tube.

(2) DNA Amplification Procedure

Long PCR Method

Reaction Mixture: 5 mM $MgCl_2$, 25 mM TAPS (pH 9.3, 25° C.), 50 mM KCl, 1 mM 2-mercaptoethanol, 0.35 mM dNTPs, 0.2 µM of forward primer, 0.2 µl of reverse primer, 0.2 µg/ml genome DNA, 2 units of LA Taq DNA polymerase (Takara), total volume 50 µl.

Reaction Cycle: The cycle of 98° C., for 20 seconds and 70° C., 12 minutes is repeated 33 times.

Primers for amplification have the following sequences:

Primer A (Forward Primer)
  5'-GGAGTAGGTCTAAGGCACGCAGTC-3' (SEQ ID NO:1)

Primer B (Reverse Primer):
  5'-TCAGACCACAGGCAGGACTTTCCGG-3' (SEQ ID NO:2)

(3) Restriction Enzyme Digestion

Composition of Reaction Mixture for Van91 I: 20 mM tris-HCl (pH 8.5), 10 mM $MgCl_2$, 1 mM DTT, 100 mM KCl Van91 I is added to the reaction mixture at a concentration of 4 units/20 µl of reaction mixture and incubation is conducted at 37° C. for 3 hours.

(4) Electrophoresis Procedure

Electrophoresis Buffer: 1×TAE (50×TAE contains 242 g of Tris base, 57.1 ml of glacial acetic acid, 50 mM EDTA per 1 l, pH 8.0)

The electrophoresis is carried out for 30 minutes at a voltage of 100 V using the above-mentioned buffer and 0.8% agarose gel (AGAROSE Type 1, SIGMA). Then, the gel is stained with ethidium bromide solution (5 µg/ml) for 5 minutes, and washed with distilled water for 5 minutes. DNA bands revealed by UV exposure are observed.

(5) Determination of Genotype

When the amplification is carried out using primer A and primer B and the obtained DNA fragment is treated with Van91 I, the bands obtained by electrophoresis are as follows:

about 3.5 kb (overlap of 3.4 kb and 3.5 kb) and about 2.5 kb (genotype VV)

about 3.4 kb, about 3.3 kb and about 2.5 kb (genotype vv)

about 3.5 kb (overlap of 3.4 kb and 3.5 kb), about 3.3 kb and about 2.5 kb (genotype Vv) (See FIG. 1)

Example 1

V-v type genotypes were determined in accordance with the above-mentioned procedure in 712 hemodialyzed Japanese patients and 106 healthy Japanese, all of them being randomly selected. The frequency of each genotype is shown in Table 1. The total frequency of VV genotype and Vv genotype is about 25%.

TABLE 1

|  | Number of Samples | vv | Vv | VV |
|---|---|---|---|---|
| Hemodialyzed Patients | 712 | 531 (71.4%) | 157 (22.0%) | 24 (3.4%) |
| Healthy Subjects | 106 | 82 (77.4%) | 21 (19.8%) | 3 (2.8%) |
| Total | 818 | 613 (74.9%) | 178 (21.8%) | 27 (3.3%) |

17 subjects (Vv and vv genotype) were selected from the above 106 healthy subjects, and the relationship between genotype and PTH reactivity was examined. PTH reactivity was determined by measuring the change of cAMP level in urine by the Ellsworth-Howard test.

Ellsworth-Howard Test

At the beginning of the test, subjects urinate and drink 200 ml of water. One hour later they drink 200 ml of water, and after another one hour again they drink 200 ml of water. Then, urine is collected and measured in quantity, and 5 ml of blood is collected. Then, 100 units of PTH (Human PTH Inj. ASAHI KASEI, 100 units of teriparatide acetate) are injected intravenously. 15 minutes later, 5 ml of blood is collected, and 45 minutes after blood collection they drink 200 ml of water, and one hour after this urine is collected and measured in quantity. In urine collected before and after PTH injection, the levels of cAMP, creatinine, calcium and inorganic phosphate are measured. In serum collected before and after PTH injection, the levels of calcium ion, creatinine, calcium and inorganic phosphate are measured. The measurement of cAMP level is carried out by the radioimmunoassay-dextran coated charcoal method. An increased level of ΔcAMP indicates high PTH reactivity.

Results

Figure 2:
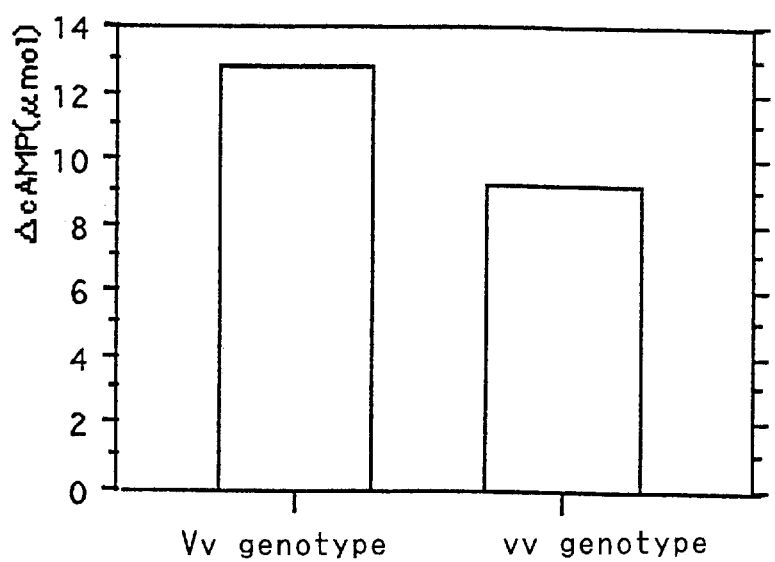
FIG. 2 is a graph showing ΔcAMP, an indicator of PTH reactivity, in each genotype.

The results obtained by measurement of ΔcAMP level in urine are shown in each genotype (FIG. 2). As is apparent from FIG. 2, PTH reactivity in Vv genotype is significantly higher than PTH reactivity in vv genotype. Also, the total frequency of VV and Vv genotypes is about 25% as mentioned above, and therefore, Van91 I polymorphism of the PTHR gene in Japanese satisfies the definition of genetic polymorphism. Thus, analysis of polymorphism of PTHR gene results in the prediction of PTH reactivity.

Example 2

In 661 hemodialyzed patients, PTHR gene polymorphism was analyzed using restriction enzyme Van91 I by the above-mentioned method. Also, the serum PTH level in each patient was measured.

As a result, the serum intact PTH level was 129±162 pg/ml in vv genotype (n=494), 167±200 pg/ml in Vv genotype (n=146), and 136±175 pg/ml in VV genotype (n=21). According to a Fisher dispersion analysis, there was a significant difference between vv genotype and Vv genotype ($p<0.05$). According to a Mann-Whitney test of vv genotype and (Vv+VV) genotypes, there was also a significant difference. Therefore, it is apparent that polymorphism in the PTHR gene is strongly associated with the severity of secondary hyperparathyroidism.

From the results of Example 1 and Example 2 shown above, the PTHR gene has genetic polymorphism, and this polymorphism is associated with PTH reactivity and also associated with severity of hyperparathyroidism.

According to the method of the present invention, PTH reactivity can be predicted by analysis of polymorphism in the parathyroid hormone receptor gene. Also, this analysis of polymorphism enables the prediction of the tendency for hemodialyzed patients to develop severe secondary hyperparathyroidism, and the prediction of the tendency for humans to develop primary hyperparathyroidism. Therefore, a suitable therapeutic method can be selected to prevent severity. Furthermore, the prediction of PTH reactivity can be used in predicting the effects of PTH to be administered for treatment of regressive osteoporosis and selecting a suitable method for treatment.

What is claimed is:

1. A method for predicting reactivity to parathyroid hormone in a human, comprising determining a genotype in the parathyroid hormone receptor gene with respect to Van91 I polymorphism, thereby predicting the reactivity to parathyroid hormone, wherein detection of the VV or Vv genotype in the parathyroid hormone receptor gene with respect to the Van91 I polymorphism indicates an increase in PTH reactivity relative to the vv genotype.

2. The method according to claim 1, wherein the genotype is determined by amplifying the first intron region of the parathyroid hormone receptor gene and treating the amplified DNA fragment with restriction enzyme Van91 I to obtain the digestion pattern.

3. The method according to claim 2, wherein the amplification is carried out using a primer having the sequence of SEQ ID NO:1 and a primer having the sequence of SEQ ID NO:2.

4. A primer set for use in analyzing the Van91 I polymorphism in the parathyroid hormone receptor gene, consisting of a primer having the sequence of SEQ ID NO:1 and a primer having the sequence of SEQ ID NO:2.

5. A kit for use in predicting reactivity to parathyroid hormone in a human, comprising the primer set according to claim 4 and restriction enzyme Van91I.

6. A method for predicting reactivity to parathyroid hormone in a patient who is being treated for regressive osteoporosis by administration of parathyroid horme, comprising determining a genotype in the parathyroid hormone receptor gene with respect to Van91 I polymorphism, thereby predicting the reactivity to parathyroid hormone.

7. The method according to claim 6, wherein the genotype is determined by amplifying the first intron region of the parathyroid hormone receptor gene and treating the amplified DNA fragment with restriction enzyme Van91 I to obtain the digestion pattern.

* * * * *

SEQUENCE LISTING

<160> NUMBER OF SEQ ID NOS: 2

<210> SEQ ID NO 1
<211> LENGTH: 24
<212> TYPE: DNA

```
<213> ORGANISM: Artificial Sequence
<220> FEATURE:
<223> OTHER INFORMATION: Description of Artificial Sequence:primer
      designed for amplifying parathyroid hormone receptor gene

<400> SEQUENCE: 1
ggagtaggtc taaggcacgc agtc                                          24

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence:primer
      designed for amplifying parathyroid hormone receptor gene

<400> SEQUENCE: 2
tcagaccaca ggcaggactt tccgg                                         25
```